US010266854B2

(12) United States Patent
Lee

(10) Patent No.: US 10,266,854 B2
(45) Date of Patent: Apr. 23, 2019

(54) MICROORGANISM CAPABLE OF SIMULTANEOUS CO-FERMENTATION OF MIXED SUGARS AND PRODUCTION METHOD OF BUTANOL USING THE SAME

(71) Applicant: GS CALTEX CORPORATION, Seoul (KR)

(72) Inventor: Sang-Hyun Lee, Daejeon (KR)

(73) Assignee: GS CALTEX CORPORATION, Seoul (KR)

( * ) Notice: Subject to any disclaimer, the term of this patent is extended or adjusted under 35 U.S.C. 154(b) by 46 days.

(21) Appl. No.: 15/015,936

(22) Filed: Feb. 4, 2016

(65) Prior Publication Data

US 2016/0230196 A1 Aug. 11, 2016

(30) Foreign Application Priority Data

Feb. 11, 2015 (KR) ........................ 10-2015-0021189

(51) Int. Cl.
| | | |
|---|---|---|
| C12N 9/02 | (2006.01) | |
| C12N 9/04 | (2006.01) | |
| C12N 9/10 | (2006.01) | |
| C12P 7/16 | (2006.01) | |
| C12N 15/52 | (2006.01) | |
| C12R 1/145 | (2006.01) | |

(52) U.S. Cl.
CPC .............. *C12P 7/16* (2013.01); *C12N 9/0006* (2013.01); *C12N 9/0008* (2013.01); *C12N 9/13* (2013.01); *C12N 15/52* (2013.01); *C12R 1/145* (2013.01); *C12Y 101/01001* (2013.01); *C12Y 102/01003* (2013.01); *C12Y 208/03009* (2013.01); *Y02E 50/10* (2013.01)

(58) Field of Classification Search
CPC ......... C12P 7/16; C12R 1/145; C12N 9/0008; C12N 9/0006; C12N 9/13; C12Y 102/01003; C12Y 101/01001; C12Y 208/03009
See application file for complete search history.

(56) References Cited

FOREIGN PATENT DOCUMENTS

| CA | 2880181 A1 | 2/2014 |
|---|---|---|
| KR | 1020030074735 A | 9/2003 |
| KR | 1020110033087 A | 3/2011 |
| KR | 1020110033089 A | 3/2011 |
| WO | 2012159571 A1 | 11/2012 |

OTHER PUBLICATIONS

K. Ounine et al., 'Regulation and Butanol Inhibition of D-Xylose and D-Glucose Uptake in Clostridium acetobutylicum', Applied and Environmental Microbiology, Apr. 1985, pp. 874-878, vol. 49, No. 4, American Society of Microbiology.
Han Xiao et al., 'Confirmation and Elimination of Xylose Metabolism Bottlenecks in Glucose Phosphoenolpyruvate-Dependent Phosphotransferase System-Deficient Clostridium acetobutylicum for Simultaneous Utilization of Glucose, Xylose, and Arabinose', Applied and Environmental Microbiology, Nov. 2011, pp. 7886-7895, vol. 77, No. 22, American Society for Microbiology.
Yong Chen et al., 'Production of Butanol from Glucose and Xylose with Immobilized Cells of Clostridium acetobutylicum', Biotechnology and Bioprocess Engineering, Sep. 28, 2012, pp. 234-241.
Cong Ren et al., 'Identification and inactivation of pleiotropic regulator CcpA to eliminate glucose repression of xylose utilization in Clostridium acetobutylicum', Metabolic Engineering, Feb. 5, 2010, pp. 446-454, Elsevier Inc.
Canadian Office Action dated Jan. 24, 2017 in connection with the counterpart Canadian Patent Application No. 2,920,617.
Lee et al., "Metabolic Engineering of Clostridium acetobutylicum ATCC 824 for Isopropanol-Butanol-Ethanol Fermentation," Applied and Environmental Microbiology, vol. 78, No. 5, Mar. 2012, pp. 1416-1423.
Canadian Office Action dated Jan. 21, 2019, issued in corresponding Canadian Patent Application No. 2,920,617.

*Primary Examiner* — Delia M Ramirez
(74) *Attorney, Agent, or Firm* — Hauptman Ham, LLP

(57) ABSTRACT

Embodiments of the invention provide a microorganism capable of simultaneous co-fermentation of two or more sugars in a lignocellulosic hydrolysate and having tolerance against microorganism growth inhibitory substances in the lignocellulosic hydrolysate and further having butanol productivity. In addition, embodiments of the invention provide a recombinant microorganism in which a pathway converting butyryl-CoA into butanol or a pathway converting butyrate into butyryl-CoA is promoted, and butanol productivity is increased. Further, a method for producing butanol using the microorganisms is provided.

15 Claims, 13 Drawing Sheets

Specification includes a Sequence Listing.

MICROORGANISM CAPABLE OF SIMULTANEOUS CO-FERMENTATION OF MIXED SUGARS AND PRODUCTION METHOD OF BUTANOL USING THE SAME

CROSS REFERENCE TO RELATED APPLICATION

This application claims the benefit of Korean Patent Application No. 10-2015-0021189, filed on Feb. 11, 2015, which is hereby incorporated by reference in its entirety into this application.

BACKGROUND

1. Technical Field

The present invention relates to a microorganism capable of simultaneous co-fermentation of mixed sugars and a method for producing butanol using the same.

2. Description of the Related Art

Butanol is a chemical intermediate with a wide range of applications such as biofuels, and is thus considered very an useful chemical.

In the related art, a method for producing butanol, acetone and ethanol by fermenting sugars using *Clostridium* strains was utilized in the early 1900's. As prices for petroleum declined and butanol could be produced at low cost by an oxo process, biological methods for producing butanol are replaced by a method for producing butanol in a petrochemical way. However, due to various environmental problems including global warming and the like originating from the use of petroleum resources, there has been an increasing need for an environmentally friendly method for producing butanol through microbial fermentation with renewable sources.

However, in order to produce butanol on an industrial scale using microorganisms, it is necessary that cost for biomass to be utilized as raw materials by microorganisms is inexpensive and the biomass is a non-food resource. In practice, in the case of producing butanol using traditional starch-based resources, it is known that raw material costs account for 60% of production cost. This stems from rising crop prices and low fermentation yield of strains. Therefore, in order to produce biobutanol economically on an industrial scale, renewable, inexpensive and non-food resources can be considered as biomass. It is apparent that cellulosic biomass is the resource satisfying such conditions.

Cellulosic biomass is composed of cellulose having β-1,4 linked glucose units and hemicelluloses (arabinoxylan, galactomannan and xyloglucan) composed of various pentoses and hexoses. When cellulosic biomass is hydrolyzed, hexoses such as glucose, mannose, galactose, pentoses such as xylose, arabinose, and the like, and disaccharides, such as cellobiose are produced. Thereamong, xylose is known as the second most abundant saccharide after glucose present in cellulosic biomass. However, in the case of microorganisms, specifically *Clostridium acetobutylicum* ATCC824, it is known that metabolism of other sorts of sugars is repressed when glucose and other sorts of sugars are present simultaneously, which is referred to as carbon catabolite repression (CCR) (Ounine K, Petitdemange H, Raval G, Gay R. 1985. Appl Environ Microbiol 49:874-8). Such a CCR phenomenon inhibits complete fermentation of mixed sugars in a lignocellulosic hydrolysate and thus reduces fermentation yield, thereby reducing fermentation capabilities of the strain. For example, although *Clostridium* sp. AH-1 (FERM-P 6093 ATCC39045) can utilize arabinose and xylose, it preferentially utilizes glucose, and then arabinose and xylose. Accordingly, glucose is first consumed, and then arabinose and xylose are utilized after expressing genes required in utilization of arabinose and xylose. Thus, in the case of continuous fermentation of mixed sugars using *Clostridium* sp. AH-1 (FERM-P 6093 ATCC39045), there are problems in that not only are arabinose and xylose accumulated in a culture solution but it also takes several hours to express genes required for their utilization. Therefore, there is a need for microorganisms capable of producing butanol by simultaneously fermenting mixed sugars in a lignocellulosic hydrolysate without CCR.

With the recent development of metabolic engineering technology and complete genome sequencing of *Clostridium acetobutylicum*, continuous efforts have been focused on more effective production of butanol. Further, studies relating to engineering of metabolic pathways have been actively performed. For example, reports say that, when a catabolite control protein A (ccpA) gene of *Clostridium acetobutylicum* is deleted, CCR phenomenon is alleviated, thereby allowing simultaneous co-fermentation of glucose and xylose (Ren C, Gu Y, Hu S, Wu Y, Wang P, et al. 2010. Metabolic Engineering 12:446-54). However, in this case, the degree of co-fermentation of glucose and xylose is negligible and the capabilities of the strain are not sufficient in terms of applicability on an industrial scale. Further, reports say that, when a gene encoding enzyme II of the D-glucose phosphoenolpyruvate-dependent phosphotransferase system (PTS) of *Clostridium acetobutylicum* is deleted and xylose transferase, xylose isomerase and xylulose 5-phosphatase (xylose kinase) are expressed, CCR is alleviated, thereby allowing simultaneous co-fermentation of glucose and xylose to produce butanol (Xiao H, Gu Y, Ning Y, Yang Y, Mitchell W J, et al. 2011. Appl Environ Microbiol 77:7886-95). However, this process also has limits in terms of commercial applicability since only about 5 g/L of xylose can be simultaneously co-fermented (namely, simultaneous co-fermentation of xylose is low), and productivity (0.31 g/L/h) and yield (16% (wt/wt)) are very low.

Furthermore, a lignocellulosic hydrolysate produced by pretreatment of cellulosic biomass including woody biomass or grass type biomass such as wood, empty fruit bunch (EFB), corn stalk, rice straw, and the like (hereinafter referred to as "lignocellulosic biomass") contains unknown substances which may cause side-reactions during pretreatment of lignocellulosic biomass by acids or bases during saccharification, thereby inhibiting growth of microorganisms. Accordingly, in order to effectively ferment mixed sugars simultaneously, genetic engineering for simultaneous co-fermentation of mixed sugars as well as microorganisms having tolerance against inhibitory substances should be developed at the same time. However, microorganisms having tolerance against inhibitory substances and capable of simultaneous co-fermentation of mixed sugars on a commercially applicable scale have not yet been developed.

BRIEF SUMMARY

It is an aspect of the present invention to provide a butanol producing strain having tolerance against a lignocellulosic hydrolysate and capable of simultaneous co-fermentation of mixed sugars.

In accordance with one aspect of the present invention, there is provided a microorganism capable of simultaneous co-fermentation of two or more sugars in a lignocellulosic hydrolysate and having butanol productivity.

The microorganism according to the present invention can produce butanol with high selectivity by simultaneously co-fermenting mixed sugars in hydrolysate of lignocellulosic biomass.

BRIEF DESCRIPTION OF THE DRAWINGS

The above and other aspects, features, and advantages of the present invention will become apparent from the detailed description of the following embodiments in conjunction with the accompanying drawings, in which.

DETAILED DESCRIPTION

Figure 1:
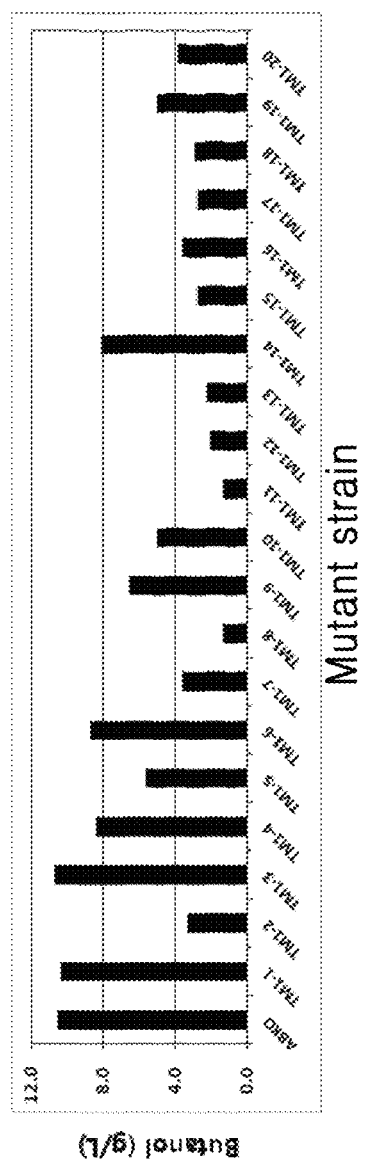
FIG. 1 shows butanol productivity of TM1-1 to TM1-20 which is a lignocellulosic hydrolysate tolerant strains.

The present invention relates to a microorganism capable of simultaneous co-fermentation of two or more sugars in a lignocellulosic hydrolysate hydrolysate and having butanol productivity.

In addition, the present invention relates to a method for producing butanol, including: preparing a medium including two or more sugars; inoculating the medium with a microorganism; and culturing the microorganism.

Further, the present invention relates to a recombinant microorganism capable of simultaneous co-fermentation of two or more sugars in a lignocellulosic hydrolysate and having butanol productivity, wherein a pathway converting butyryl-CoA into butanol or a pathway converting butyrate into butyryl-CoA is promoted, and butanol productivity is increased.

Furthermore, the present invention relates to a method for producing butanol, including: preparing a medium including two or more sugars; inoculating the medium with a recombinant microorganism according to the present invention; and culturing the recombinant microorganism.

Hereinafter, the present invention will be described in detail.

Microorganism Capable of Simultaneous Co-Fermentation of Two or More Sugars in Hydrolysate of a Lignocellulosic Biomass and Having Butanol Productivity.

The present invention relates to a microorganism capable of simultaneous co-fermentation of two or more sugars in a lignocellulosic hydrolysates and having butanol productivity. The microorganism has tolerance against a lignocellulosic hydrolysate, more preferably tolerance against microorganism growth inhibitory substances in a lignocellulosic hydrolysate. Further, the microorganism is capable of simultaneous co-fermentation of glucose and xylose.

The microorganism is preferably *Clostridium acetobutylicum*, more preferably mutant *Clostridium acetobutylicum*, still more preferably mutant *Clostridium acetobutylicum* ATCC824 Δpta Δbuk. *Clostridium acetobutylicum* ATCC824 Δpta Δbuk is a recombinant microorganism in which a pta gene expressing phosphotransacetylase and a buk gene expressing butyrate kinase in *Clostridium acetobutylicum* ATCC824 are deleted at the same time.

Preferably, the microorganism is *Clostridium acetobutylicum* TM2-1-C (accession number KCTC 12604BP).

Lignocellulosic Hydrolysate

The microorganism according to the present invention has tolerance against a lignocellulosic hydrolysate and is capable of simultaneous co-fermentation of two or more sugars in the lignocellulosic hydrolysate. The lignocellulosic hydrolysate is hydrolysates obtained by hydrolyzing lignocellulosic raw materials (for example, wood, EFB (empty fruit bunch), corn stalks, sugarcane stalks, rice straw, and the like), preferably hydrolysates obtained by hydrolyzing lignocellulosic materials and removing lignin. The lignocellulosic hydrolysate contains mixed sugars comprised of two or more sugars. Preferably, the hydrolysate contains pentoses, hexoses and disaccharides such as glucose, xylose, mannose, galactose, arabinose, cellobiose, and the like, and particularly has high content of glucose and xylose.

Tolerance Against a Lignocellulosic Hydrolysate

The microorganism according to the present invention has tolerance against the lignocellulosic hydrolysate. Tolerance against the lignocellulosic hydrolysate means that the microorganism is able to grow in a medium including the hydrolysate, and growth inhibition of the microorganism due to a substance in the does not occur.

Simultaneous Co-Fermentation Capability

The microorganism according to the present invention is capable of simultaneous co-fermentation of two or more sugars in a lignocellulosic hydrolysate. The term "capable of simultaneous co-fermentation" means that fermentation of one sugar is not preferred to fermentation of other sugars. Since the microorganism according to the present invention is capable of simultaneous co-fermentation of two or more sugars, a phenomenon that metabolism of one sugar is suppressed by metabolism of the other sugar is prevented between the sugars to be simultaneously co-fermented.

Recombinant Microorganism

The present invention relates to a recombinant microorganism capable of simultaneous co-fermentation of two or more sugars in the lignocellulosic hydrolysate and having butanol productivity, wherein a pathway converting butyryl-CoA into butanol or a pathway converting butyrate into butyryl-CoA is promoted, and butanol productivity is increased.

The recombinant microorganism may have an increased CoA transferase activity, which leads to an accelerated pathway converting butyrate into butyryl-CoA or an increased aldehyde/alcohol dehydrogenase activity converting butyryl-CoA into butanol. The recombinant microorganism is capable of simultaneous co-fermentation of two or more sugars in the lignocellulosic hydrolysate, through which produces ABE (acetone, butanol, and ethanol) with particularly high productivity and selectivity of butanol.

Acceleration of Pathway Converting Butyryl-CoA into Butanol

Butyryl-CoA may be converted into butanol via butanal in butanol production pathway. The pathway may be accelerated by promoting the step of converting butyryl-CoA into butanal or the step of converting butanal into butanol. Each step may be accelerated by utilizing a known method such as increasing enzyme activity.

For example, aldehyde/alcohol dehydrogenase regulates conversion of butyryl-CoA into butanal and conversion of butanal into butanol. The pathway converting butyryl-CoA into butanol may be accelerated by increasing aldehyde/alcohol dehydrogenase activity. The increase of aldehyde/alcohol dehydrogenase activity may be performed by increasing expression and enzyme activity of aldehyde/alcohol dehydrogenase, and the like. For example, a person skilled in the art may increase aldehyde/alcohol dehydrogenase activity by selecting an appropriate method such as introduction, amplification, rearrangement of adhE gene encoding aldehyde/alcohol dehydrogenase, or regulation of gene expression in the course of transcription or translation, and the like.

Acceleration of Pathway Converting Butyrate into Butyryl-CoA

CoA transferase regulates conversion of butyrate into butyryl-CoA in butanol production pathway. The pathway converting butyrate into butyryl-CoA may be accelerated by increasing the activity of CoA transferase. Increase in activity of CoA transferase may be performed by increasing expression and enzyme activity of CoA transferase, and the like. For example, a person having ordinary knowledge in the art can increase CoA transferase activity by selecting an appropriate method such as introduction, amplification, rearrangement of cftA or ctfB (hereinafter referred to as "ctfAB") gene encoding CoA transferase, or regulation of gene expression in the course of transcription or translation, and the like.

Simultaneous Co-Fermentation of Recombinant Microorganism

The recombinant microorganism according to the present invention is capable of simultaneous co-fermentation of two or more sugars in a lignocellulosic hydrolysate. Preferably, the recombinant microorganism according to the present invention is capable of simultaneous co-fermentation of glucose and at least one sugar selected from the group consisting of xylose, arabinose and cellobiose. More preferably, the recombinant microorganism according to the present invention is capable of simultaneous co-fermentation of xylose at a ratio of 90% or more, preferably 95% or more. Still more preferably, the recombinant microorganism according to the present invention is capable of simultaneous co-fermentation of arabinose at a ratio of 90% or more, preferably 95% or more, still more preferably 98% or more. More preferably, the recombinant microorganism according to the present invention is capable of simultaneous co-fermentation of cellobiose at a ratio of 85% or more, preferably 90% or more, still more preferably 92% or more. The ratio of simultaneous co-fermentation refers to a value obtained by dividing a difference between the amount of sugars in the hydrolysate provided to a medium and the amount of sugars remaining after continuous fermentation.

Ratio of simultaneous co-fermentation (%)={(Total sugars introduced (g)−amount of sugars remaining after fermentation (g))/Total sugars introduced (g)}×100

Ex) Ratio of simultaneous co-fermentation of xylose (%)

Ratio of simultaneous co-fermentation of xylose={(Total xylose introduced (g)−amount of sugars remaining after fermentation (g))/(Total xylose introduced (g))}×100

Butanol Productivity of Recombinant Microorganism

The recombinant microorganism according to the present invention ferments two or more sugars in a lignocellulosic hydrolysate, thereby producing ABE with particularly high butanol productivity.

The recombinant microorganism according to the present invention exhibits butanol selectivity of 70% or more, preferably 75% or more, based on fed-batch cultivation. Further, the recombinant microorganism according to the present invention exhibits acetone selectivity less than 20%, preferably less than 15%, more preferably less than 13%, based on fed-batch cultivation. In addition, the recombinant microorganism according to the present invention exhibits ethanol selectivity less than 20%, preferably less than 15%, more preferably less than 13%, based on fed-batch cultivation.

The recombinant microorganism according to the present invention exhibits butanol productivity of 0.5 g/L/h or more, or 0.8 g/L/h or more, or 1.0 g/L/h or more, or 1.5 g/L/h or more, or 1.8 g/L/h or more, or 2.0 g/L/h or more, based on exponential phase of strains in fed-batch cultivation.

Method for Producing Butanol Using Recombinant Microorganism

The present invention relates to a method for producing butanol by simultaneous co-fermentation of two or more sugars in a lignocellulosic hydrolysate using the recombinant microorganism according to the present invention. Further, the present invention relates to a method for producing butanol including: preparing a medium including two or more sugars; inoculating the medium with a recombinant microorganism according to the present invention; and culturing the recombinant microorganism. The two or more sugars include glucose and at least one sugars selected from the group consisting of xylose, arabinose and cellobiose. The medium preferably includes a lignocellulosic hydrolysate.

The above and other aspects, features, and advantages of the present invention will become apparent from the detailed description of the following embodiments in conjunction with the accompanying drawings. However, it should be underleft that the present invention is not limited to the following embodiments and may be embodied in different ways, and that the embodiments are provided for complete disclosure and thorough understanding of the invention by those skilled in the art. The scope of the invention should be defined only by the accompanying claims and equivalents thereof.

Materials and Methods

Wild-type strain *Clostridium acetobutylicum* ATCC824 was purchased from the American Type Culture Collection (ATCC).

A gene deleted strain *Clostridium acetobutylicum* ATCC824 Δpta Δbuk (hereinafter referred to as "ABKO") was prepared using *Clostridium acetobutylicum* ATCC824 in accordance with the method disclosed in WO2011/037415. The mutant ABKO is a strain having butanol productivity.

Methyl-N-Nitro-N-nitrosoguanidine (MNTG) to be used as a mutagen to cause random genetic mutation of genes was purchased from TCI (Tokyo Chemical Industry, Japan).

On evaluating biobutanol productivity of *C. acetobutylicum* strain, selectivity for specific product (proportion of a specific product in the produced mixed products (ABE:

acetone, butanol, ethanol)), butanol productivity and yield were calculated as below:

Butanol selectivity (%): (Produced amount of butanol (g)/produced amount of ABE (g))×100

Ethanol selectivity (%): (Produced amount of ethanol (g)/produced amount of ABE (g))×100

Acetone selectivity (%): (Produced amount of acetone (g)/produced amount of ABE (g))×100

Butanol productivity (g/L/h): Amount of butanol produced per hour per unit volume (Butanol productivity in batch culture and fed-batch culture method is based on exponential phase of solvent production. In continuous culture, butanol productivity is based on cumulative amount of ABE produced in total phase.)

Yield (%): (Produced amount of ABE (g)/carbon source (g))×100

ABE productivity (g/L/h): Amount of ABE produced per hour per unit volume

The hydrolysates used in Experimental Examples were prepared by the following method.

To a reactor containing 70% sulfuric acid, chopped waste wood was added and reacted at about 100° C. for 30 minutes while stirring, thereby performing pretreatment. To the pretreated slurry, a suitable amount of water was added to perform hydrolysis. In the hydrolyzed solution, various sugars including glucose, xylose, and the like derived from cellulose and hemicellulose are present in the form of mixtures (hereinafter, the mixture of sugars is referred to as "mixed sugars"). The hydrolyzed solution was pressed using a filter press at a pressure of about 3 bar such that mixed sugars could be contained in the filtrate while lignin could be separated as solid inside the filter. After removing lignin from the hydrolyzed solution, sulfuric acid was separated from the remaining solution (containing mixed sugars) using an anion exchange resin, thereby obtaining a hydrolysate having a concentration of about 100 g/L of the mixed sugars. The produced hydrolysate was concentrated again until the concentration of the mixed sugars reached about 200 g/L, and was utilized as a feeding solution for continuous cultivation.

<Experimental Example 1> Construction of Strains Having Tolerance Against the Lignocellulosic Hydrolysate <1-1> Random Mutagenesis ABKO strains were cultivated in 60 ml of liquid CGM (*Clostridium* Growth Medium) (0.75 g/L $K_2HPO_4$, 0.75 g/L $KH_2PO_4$, 0.7 g/L, $MgSO_4 \cdot 7H_2O$, 0.017 g/L $MnSO_4 \cdot 5H_2O$, 0.01 g/L, $FeSO_4 \cdot 7H_2O$, 2 g/L $(NH_4)_2SO_2$, 1 g/L NaCl, 2 g/L asparagine, 0.004 g/L p-aminobenzoic acid, 5 g/L yeast extract, 4.08 g/L $CH_3COONa \cdot 3H_2O$, and 80 g/L glucose) at 37° C. under anaerobic conditions until absorbance at 600 nm reached 0.5 (i.e., OD600=0.5). The culture solution was centrifuged at 7000 g for 10 minutes at 4° C. The cell pellets were washed with liquid CGM three times, and then re-suspended in 50 ml of liquid CGM. Methyl-N-Nitro-N-nitrosoguanidine (MNTG) was treated to have a final concentration of 50 µg/ml, and then left at 37° C. for 20 minutes to prepare libraries of mutants with a survival ratio of about 2.5%.

<1-2> Selection of Strains Having Tolerance Against the Lignocellulosic Hydrolysate Strains prepared in the above <1-1> by random mutation were diluted. The diluted strains were streaked on 2000 solid CGMs (namely, 2000×) prepared by replacing glucose with the lignocellulosic hydrolysate to form about 100 colonies. The random mutant strains formed on the streaked solid media were cultivated under the same conditions as in <1-1> for about 2 days, and 20 colonies that survived with tolerance were selected.

<1-3> Evaluation of Butanol Productivity of Strains Having Tolerance Against the Lignocellulosic Hydrolysate Since the 20 random mutant strains selected in <1-2> could lose butanol productivity during mutagenesis, mutants maintaining butanol productivity were selected through liquid cultivation.

Disposable tubes (Falcon, U.S.) including 40 ml of CGM and 5 g/L of $CaCO_3$ was inoculated with 20 strains with tolerance against the lignocellulosic hydrolysate selected in <1-2>, and then cultured at 37° C. under anaerobic conditions set forth in <1-1> for 36 hours to identify butanol productivity. Analysis of butanol was performed by gas chromatography (Agilent, U.S.). The analysis conditions are shown in Table 1.

Further, analysis of sugars was performed by liquid chromatography, in which 0.01N $H_2SO_4$ solution was used as a mobile phase and Aminex87H (Bio-Rad, U.S.) was employed as columns.

TABLE 1

| | |
|---|---|
| Injector temperature | 320° C. |
| Detector temperature | 320° C. |
| Injector split ratio | 20/1 |
| Injection volume | 0.1 ul |
| Oven condition | 80° C./15 min |
| Air flow | 300 mL/min |
| $H_2$ flow | 30 mL/min |
| Column | Supelco CarboWAX |

The analysis results are shown in FIG. 1, in which the control group is ABKO strain. 20 random mutant strains having tolerance against microorganism growth inhibitory substances in a lignocellulosic hydrolysate were selected and designated as TM1-1 to TM1-20 (FIG. 1). Thereamong, mutant strain TM1-3 having the highest butanol productivity was employed in subsequent experiments.

Figure 2:
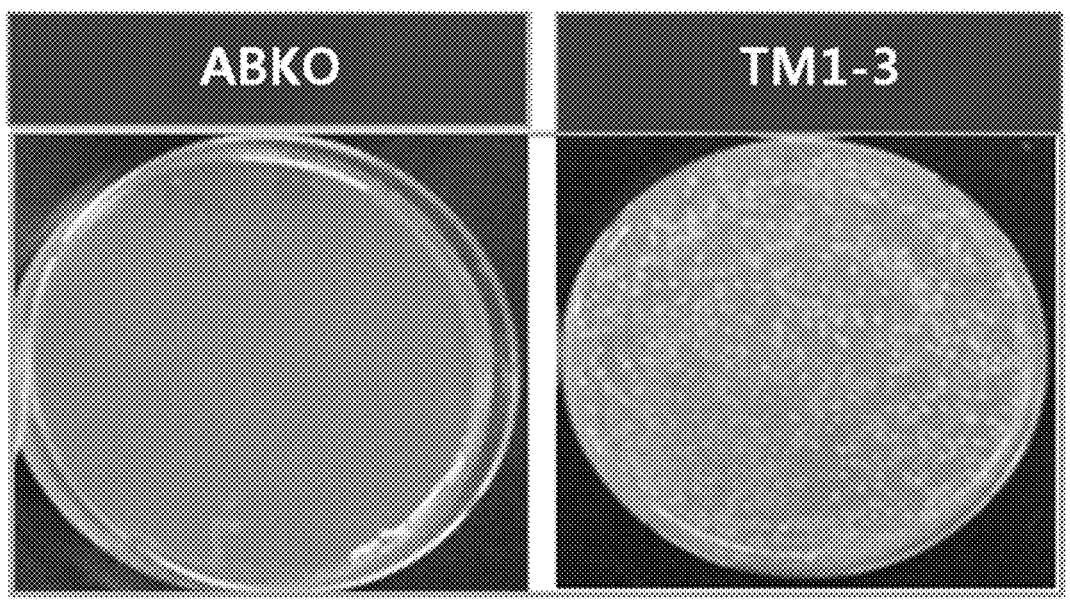
FIG. 2 shows TM1-3 strain in comparison with a control group after cultivation for 2 days in solid CGM prepared by replacing glucose with a lignocellulosic hydrolysate.

FIG. 2 shows TM1-3 in comparison with a control group after cultivation for 2 days in solid CGM prepared by replacing glucose with the lignocellulosic hydrolysate, in which the control group is ABKO. It can be seen in FIG. 2 that the control group in cultivation for 2 days showed no growth by the lignocellulosic hydrolysate, specifically microorganism growth inhibitory substances in a lignocellulosic hydrolysate, while TM1-3 grew normally.

<Experimental Example 2> Selection of Strains Capable of Simultaneous Co-Fermentation of Xylose by Batch Cultivation <2-1> Random Mutagenesis Among mutant strains prepared in <Experimental Example 1>, TM1-3 having the highest butanol productivity was employed in random mutagenesis, thereby constructing a library of the mutant. The method for constructing the mutant library was the same as that disclosed in <1-1>.

<2-2> Selection of Strains Capable of Simultaneous Co-Fermentation of Xylose and Glucose Randomly mutated strains prepared in <2-1> were diluted. The diluted strains were streaked on solid CGM prepared using 3 g/L of glucose and 3 g/L of xylose to form about 100 colonies. The random mutant strains formed on the streaked solid media were cultured under the same conditions as in <1-2> for about 2 days. 20 colonies grown rapidly were selected, and designated as TM2-1 to TM2-20.

<2-3> Evaluation of Butanol Productivity of Strains Capable of Simultaneous Co-Fermentation of Xylose and Glucose Since the 20 random mutant strains selected in <1-2> could lose butanol productivity during mutagenesis, mutants maintaining butanol productivity were selected through liquid cultivation. A detailed method for selection is as follows.

Disposable tubes (Falcon, U.S.) including 40 ml of CGM and 5 g/L of $CaCO_3$ were inoculated with 20 strains (TM2-1 to TM2-20) prepared in <2-2>, and then cultured at 37° C. under anaerobic conditions set forth in <1-1> for 36 hours to identify butanol productivity. Analysis of butanol was performed using gas chromatography (Agilent, U.S.).

Figure 3:
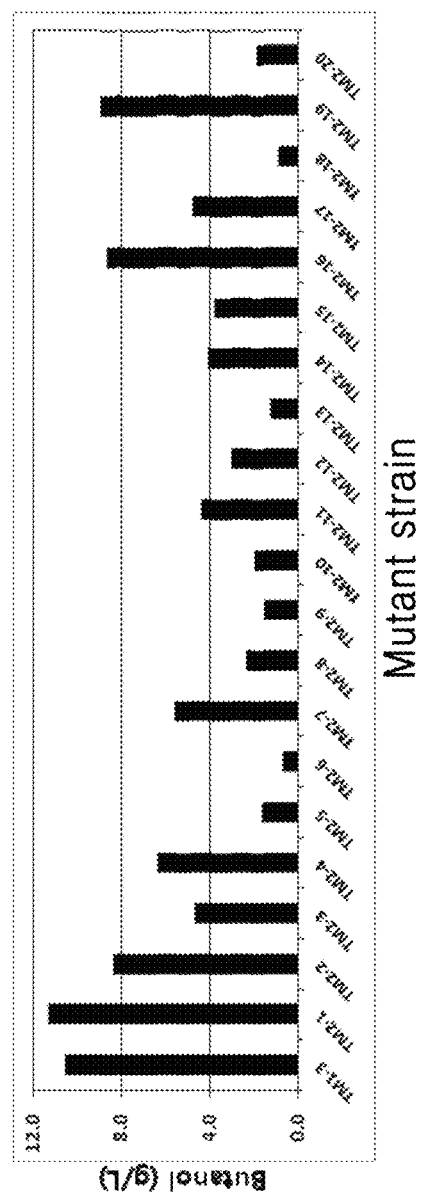
FIG. 3 shows butanol productivity of TM2-1 to TM2-20 which are xylose-glucose simultaneous co-fermenting strains.
Figure 4A:
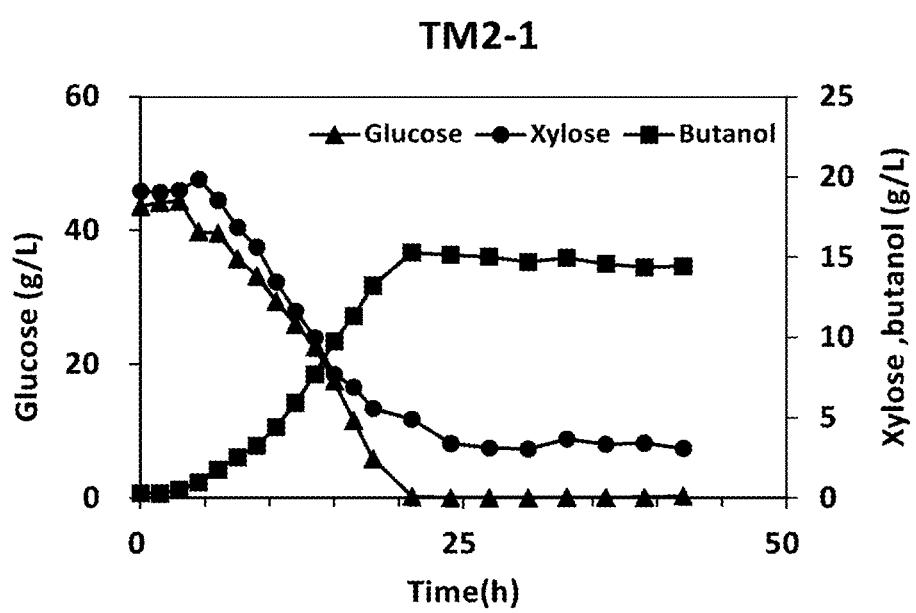
FIGS. 4a to 4e show simultaneous co-fermentation of glucose and xylose by TM2-1, TM2-16 and TM2-19.
Figure 4B:
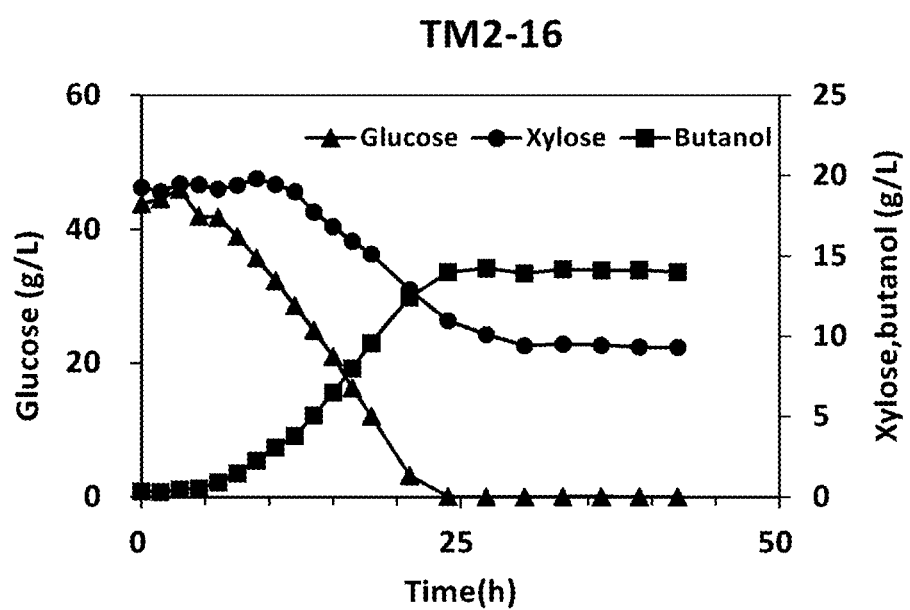
Figure 4C:
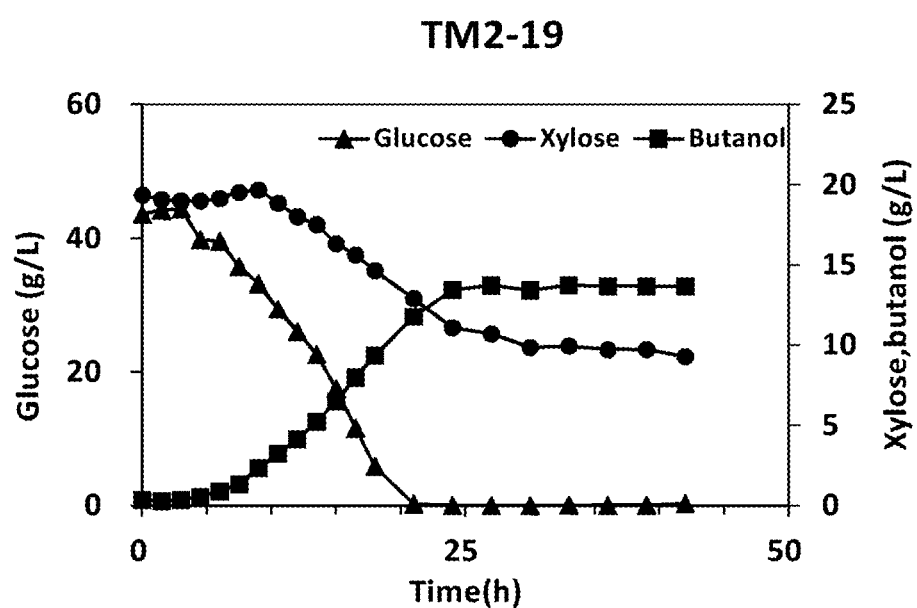
Figure 4D:
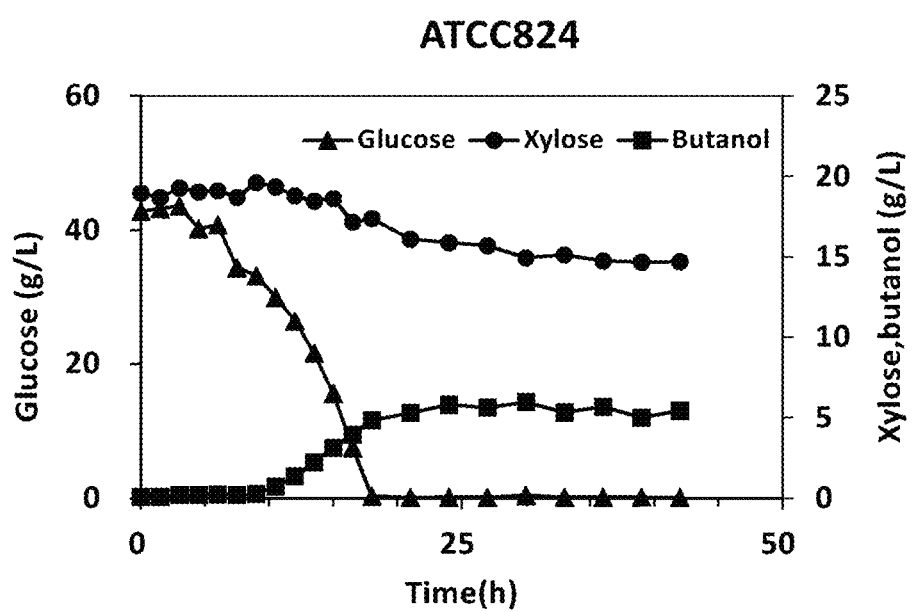
Figure 4E:
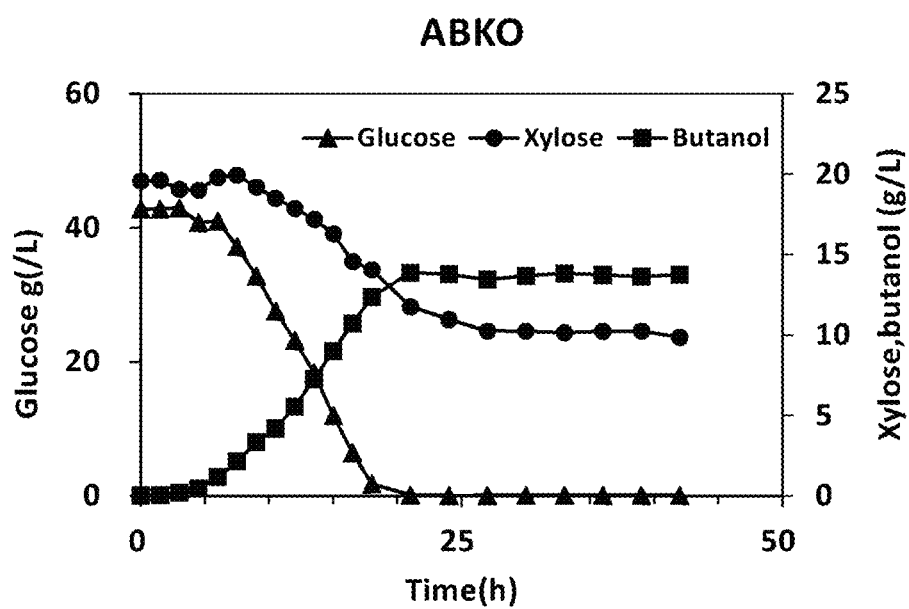

As a result, it could be seen that mutant strains TM2-1, TM2-16 and TM2-19 showed butanol productivity similar to the control group TM1-3 (FIG. 3).

<2-4> Evaluation of Simultaneous Co-Fermentation of Glucose and Xylose

Among tolerable strains considered as having butanol productivity similar to the control group in <2-3>, evaluation of simultaneous co-fermentation of glucose and xylose was performed for strains TM2-1, TM2-16 and TM2-19 by batch fermentation. A medium containing liquid CGM and mixed sugars (45 g/L glucose, 20 g/L xylose; proportion of xylose about 30% by weight) was used as the fermentation medium. Analysis of sugars was performed using liquid chromatography.

Results are shown in FIG. 4a-e. Among the strains, it was determined that strain TM2-1 was excellent in terms of simultaneous co-fermentation of glucose and xylose.

Butanol productivity and simultaneous co-fermentation of strain TM2-1 were evaluated using mixed sugars containing 40% by weight of xylose (28 g/L xylose/42 g/L glucose).

Figure 5:
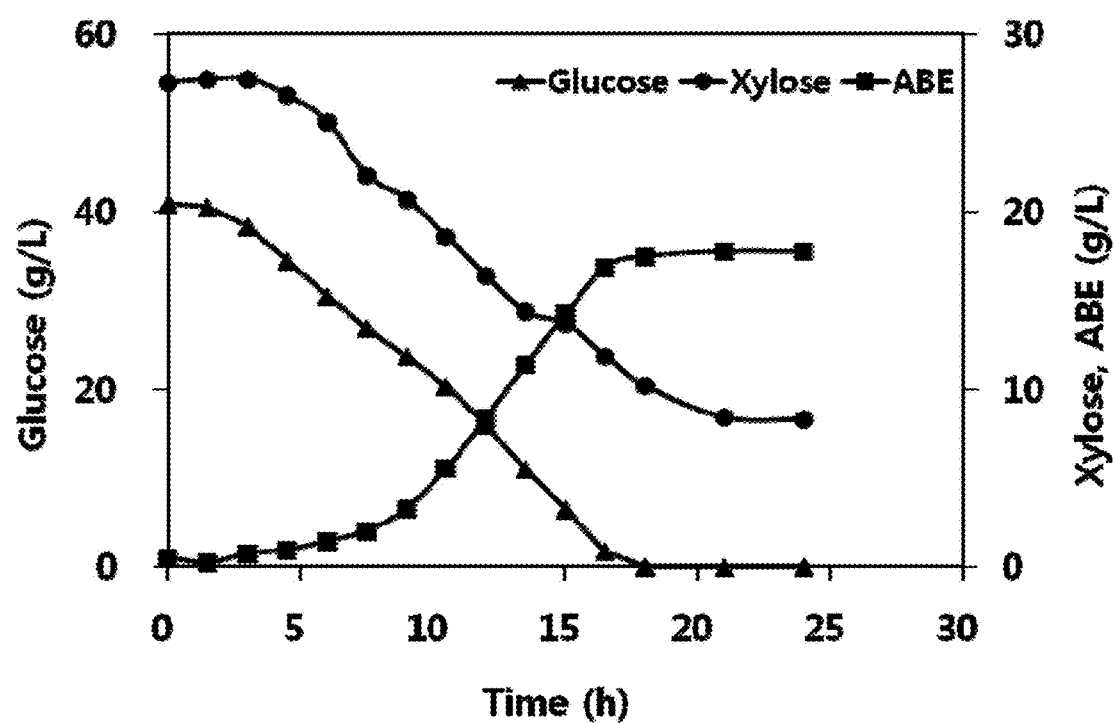
FIG. 5 shows simultaneous co-fermentation of TM2-1 in a medium containing 40% xylose.

Results are shown in FIG. 5. It can be found that strain TM2-1 showed very high proportion of xylose metabolism reaching 31% in total metabolized sugars (40.9 g/L glucose, 19.0 g/L xylose) even when mixed sugars containing a high concentration of xylose was utilized for 21 hours. Namely, about 68% of xylose introduced for 21 hours (28 g/L) was converted into ABE by simultaneous co-fermentation.

Stain TM2-1 was deposited on Jun. 9, 2014 with the International Patent Organism Depositary, Korea Collection for Type Culture (KCTC) with a deposit number of KCTC 12604BP and a designated name "TM-2-1C". Hereinafter, experiments of simultaneous co-fermentation of mixed sugars were performed using strain TM2-1-C.

<Experimental Example 3> Preparation of Strain TM2-1-C (E1AB)

Based on disclosure of International Patent Applications PCT/KR2013/001951 and PCT/KR2013/001954, pGS1-E1AB was prepared.

According to these publications, when adhE1 gene (aldehyde alcohol dehydrogenase) and cdAB gene (Co-A transferase) were overexpressed in strain ABKO (*Clostridium acetobutylicum* ATCC824 Δpta Δbuk), it was reported that ethanol productivity was reduced while butanol productivity was increased. Accordingly, simultaneous co-fermentation of mixed sugars in the lignocellulosic hydrolysate, and productivity of butanol, acetone and ethanol were evaluated by overexpressing adhE1 gene and ctfAB gene in the strain TM2-1-C.

<3-1> Preparation of pGS1-E1AB Plasmid

Figure 6:
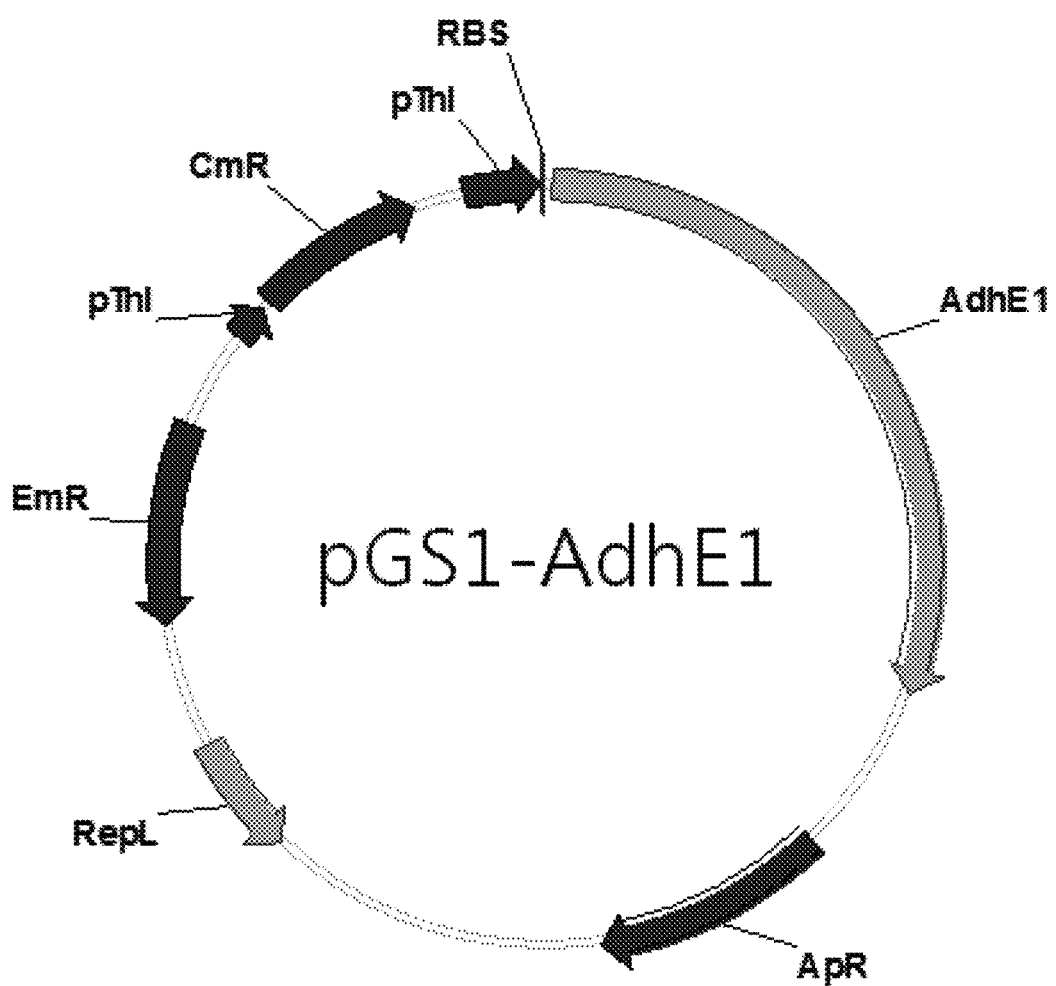
FIG. 6 shows a pGS1-AdhE1 plasmid.

*Clostridium acetobutylicum* ATCC824 was streaked on solid RCM, followed by anaerobic culturing for 24 hours. A colony selected from the streaked solid medium was cultured in 3 ml of a liquid culture medium for 18 hours, followed by centrifuging the culture solution to obtain cells. The cells were washed with 10 ml of Tris buffer, followed by purification using a Wizard Genomic DNA purification Kit (manufactured by Promega Corp., U.S.) to isolate chromosomes of the strain.

adhE1 gene (SEQ ID NO: 1) was amplified using primers AdhE1-UP-PstI (SEQ ID NO: 2) and AdhE1-DN-XhoI (SEQ ID NO: 3) and using the isolated chromosome as a template (Table 2). 100 μl of PCR reaction mixture was prepared by adding 250 μM dNTP, 20 pmol of each primer, 1.5 mM $MgCl_2$, 10 μl of 10 buffer, 100 ng of DNA template, and 1 unit of pfu polymerase. In the PCR reaction, the reaction repeated 30 cycles consisting of initial denaturing at 95° C. for 5 minutes, followed by denaturing at 95° C. for one minute, annealing at 50° C. for one minute and then polymerizing at 72° C. for one minute. The amplified gene was purified on a 1% agarose gel, and then digested with PstI and XhoI restriction enzymes to cleave a DNA fragment. The digested DNA fragment was ligated to pGS1-MCS (PCT/KR2013/001951 and PCT/KR2013/001954) digested with the same restriction enzymes, to construct pGS1-AdhE1 (FIG. 6).

TABLE 2

| | |
|---|---|
| SEQ ID NO: 1 | ATGAAAGTCACAACAGTAAAGGAATTAGATGAAAAACTCAAGGTAATTAAAGAAGCTCAAAAAAA<br>ATTCTCTTGTTACTCGCAAGAAATGGTTGATGAAATCTTTAGAAATGCAGCAATGGCAGCAATCG<br>ACGCAAGGATAGAGCTAGCAAAAGCAGCTGTTTGGAAACCGGTATGGGCTTAGTTGAAGACAAGG<br>TTATAAAAAATCATTTTGCAGGCGAATACATCTATAACAAATATAAGGATGAAAAAACCTGCGGT<br>ATAATTGAACGAAATGAACCCTACGGAATTACAAAAATAGCAGAACCTATAGGAGTTGTAGCTGC<br>TATAATCCCTGTAACAAACCCCACATCAACAACAATATTTAAATCCTTAATATCCCTTAAAACTA<br>GAAATGGAATTTTCTTTTCGCCTCACCCAAGGGCAAAAAAATCCACAATACTAGCAGCTAAAACA<br>ATACTTGATGCAGCCGTTAAGAGTGGTGCCCCGGAAAATATAATAGGTTGGATAGATGAACCTTC<br>AATTGAACTAACTCAATATTTAATGCAAAAAGCAGATATAACCCTTGCAACTGGTGGTCCCTCAC<br>TAGTTAAATCTGCTTATTCTTCCGGAAAACCAGCAATAGGTGTTGGTCCGGGTAACACCCCAGTA<br>ATAATTGATGAATCTGCTCATATAAAAATGGCAGTAAGTTCAATTATATTATCCAAAACCTATGA<br>TAATGGTGTTATATGTGCTTCTGAACAATCTGTAATAGTCTTAAAATCCATATATAACAAGGTAA<br>AAGATGAGTTCAAGAAAGAGGAGCTTATATAATAAAGAAAAACGAATTGGATAAAGTCCGTGAA<br>GTGATTTTTAAAGATGGATCCGTAAACCCTAAAATAGTCGGACAGTCAGCTTATACTATAGCAGC<br>TATGGCTGGCATAAAAGTACCTAAAACCACAAGAATATTAATAGGAGAAGTTACCTCCTTAGGTG<br>AAGAAGAACCTTTTGCCCACGAAAAACTATCTCCTGTTTTGGCTATGTATGAGGCTGACAATTTT<br>GATGATGCTTTAAAAAAAGCAGTAACTCTAATAAACTTAGGAGGCCTCGGCCATACCTCAGGAAT<br>ATATGCAGATGAAATAAAAGCACGAGATAAAATAGATAGATTTAGTAGTGCCATGAAAACCGTAA |

TABLE 2-continued

```
GAACCTTTGTAAATATCCCAACCTCACAAGGTGCAAGTGGAGATCTATATAATTTTAGAATACCA
CCTTCTTTCACGCTTGGCTGCGGATTTTGGGGAGGAAATTCTGTTTCCGAGAATGTTGGTCCAAA
ACATCTTTTGAATATTAAAACCGTAGCTGAAAGGAGAGAAAACATGCTTTGGTTTAGAGTTCCAC
ATAAAGTATATTTTAAGTTCGGTTGTCTTCAATTTGCTTTAAAAGATTTAAAAGATCTAAAGAAA
AAAAGAGCCTTTATAGTTACTGATAGTGACCCCTATAATTTAAACTATGTTGATTCAATAATAAA
AATACTTGAGCACCTAGATATTGATTTTAAAGTATTTAATAAGGTTGGAAGAGAAGCTGATCTTA
AAACCATAAAAAAAGCAACTGAAGAAATGTCCTCCTTTATGCCAGACACTATAATAGCTTTAGGT
GGTACCCCTGAAATGAGCTCTGCAAAGCTAATGTGGGTACTATATGAACATCCAGAAGTAAAATT
TGAAGATCTTGCAATAAAATTTATGGACATAAGAAAGAGAATATATACTTTCCCAAAACTCGGTA
AAAAGGCTATGTTAGTTGCAATTACAACTTCTGCTGGTTCCGGTTCTGAGGTTACTCCTTTTGCT
TTAGTAACTGACAATAACACTGGAAATAAGTACATGTTAGCAGATTATGAAATGACACCAAATAT
GGCAATTGTAGATGCAGAACTTATGATGAAAATGCCAAAGGGATTAACCGCTTATTCAGGTATAG
ATGCACTAGTAAATAGTATAGAAGCATACACATCCGTATATGCTTCAGAATACACAAACGGACTA
GCACTAGAGGCAATACGATTAATATTTAAATATTTGCCTGAGGCTTACAAAAACGGAAGAACCAA
TGAAAAAGCAAGAGAGAAAATGGCTCACGCTTCAACTATGGCAGGTATGGCATCCGCTAATGCAT
TTCTAGGTCTATGTCATTCCATGGCAATAAAATTAAGTTCAGAACACAATATTCCTAGTGGCATT
GCCAATGCATTACTAATAGAAGAAGTAATAAAATTTAACGCAGTTGATAATCCTGTAAAACAAGC
CCCTTGCCCACAATATAAGTATCCAAACACCATATTTAGATATGCTCGAATTGCAGATTATATAA
AGCTTGGAGGAAATACTGATGAGGAAAGGTAGATCTCTTAATTAACAAAATACATGAACTAAAA
AAAGCTTTAAATATACCAACTTCAATAAAGGATGCAGGTGTTTTGGAGGAAAACTTCTATTCCTC
CCTTGATAGAATATCTGAACTTGCACTAGATGATCAATGCACAGGCGCTAATCCTAGATTTCCTC
TTACAAGTGAGATAAAAGAAATGTATATAAATTGTTTTAAAAAACAACCTTAA
```

| SEQ ID NO: 2 | AdhE1-UP-PstI: | 5'-CACCTGCAGATGAAAGTCACAACAGTAAAGGAATTAGAT-3' |
|---|---|---|
| SEQ ID NO: 3 | AdhE1-DN-XhoI: | 5'-CACCTCGAGTTAAGGTTGTTTTTAAAACAATTTATATACA-3' |

Figure 7:
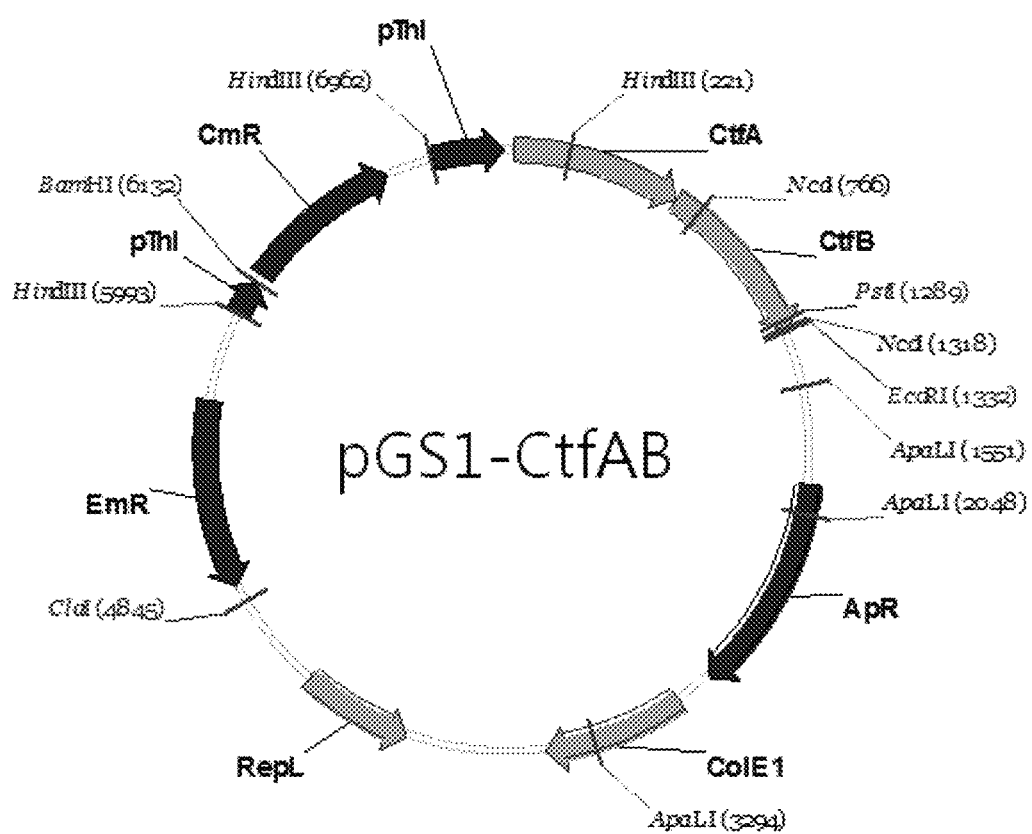
FIG. 7 shows a pGS1-CtfAB plasmid.

On the other hand, pGS1-CtfAB was prepared by introducing ctfAB gene to pGS1-MCS (BglII) vector, which is disclosed in PCT/KR2013/001951 and PCT/KR2013/001954. First, ctfAB gene (SEQ ID NO: 4) was amplified using primers CtfAB-UP-BglII (SEQ ID NO: 5) and CtfAB-DN-EcoRI (SEQ ID NO: 6) and using the isolated chromosome of *Clostridium acetobutylicum* ATCC824 as a template, and cloned into pGS1-MCS to prepare pGS1-CtfAB (Table 3, FIG. 7).

Figure 8:
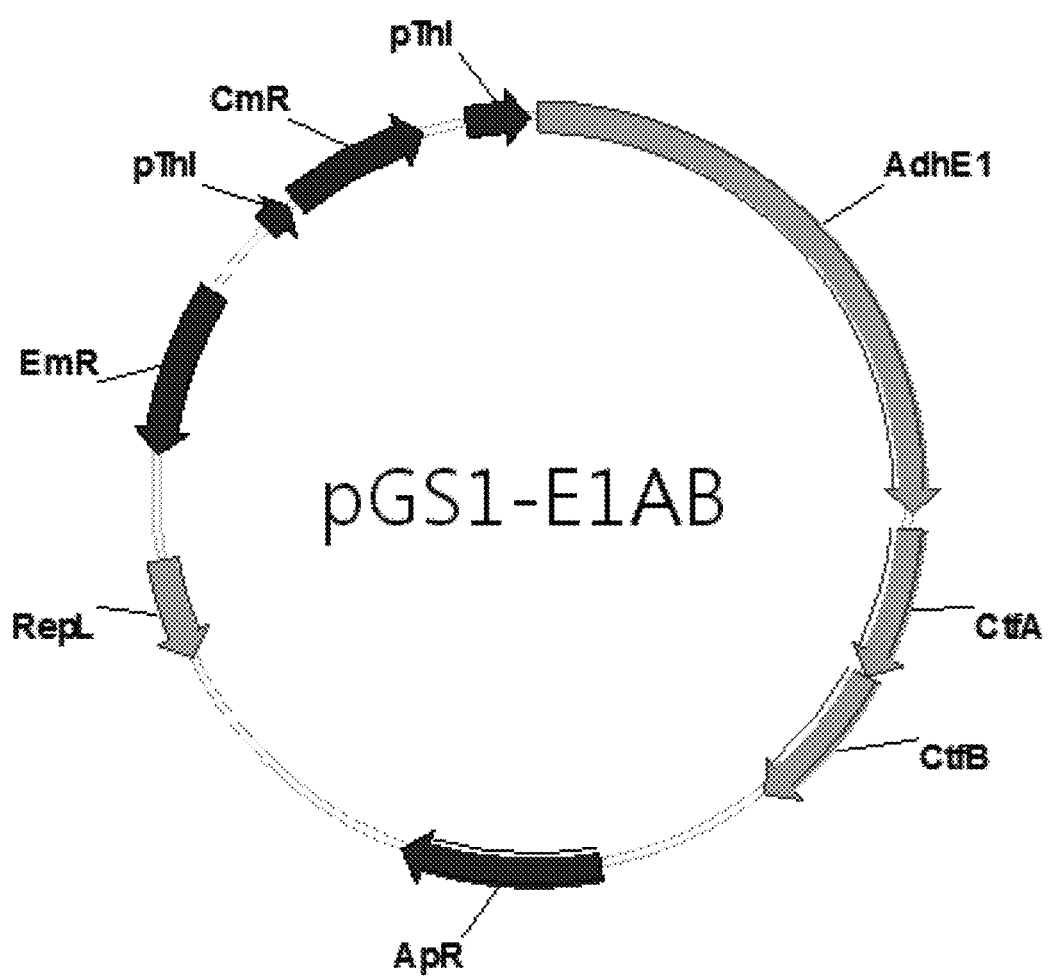
FIG. 8 shows a pGS1-E1AB plasmid.

Thereafter, ctfAB gene was amplified by PCR using primers THL-UP-XhoI (SEQ ID NO: 7) and CtfAB-DN-EcoRI (SEQ ID NO: 6) and using pGS1-CtfAB as a template. The amplified cfAB gene was purified on a 1% agarose gel, and digested with XhoI and EcoRI restriction enzymes to cleave a DNA fragment. The cleaved DNA was the ligated to a pGS1-AdhE1 vector digested with the same restriction enzymes to prepare pGS1-E1AB (FIG. 8).

<3-2> Preparation of Strain TM2-1-C (pGS1-E1AB)

Strain TM2-1-C was cultivated in 60 ml of liquid CGM (*Clostridium* Growth Medium) (0.75 g/L $K_2HPO_4$, 0.75 g/L $KH_2PO_4$, 0.7 g/L, $MgSO_4.7H_2O$, 0.017 g/L $MnSO_4.5H_2O$, 0.01 g/L, $FeSO_4.7H_2O$, 2 g/L $(NH_4)_2SO_2$, 1 g/L NaCl, 2 g/L asparagine, 0.004 g/L p-aminobenzoic acid, 5 g/L yeast extract, 4.08 g/L $CH_3COONa.3H_2O$, and 80 g/L glucose) under anaerobic conditions until absorbance at 600 nm reached 0.5 (i.e., OD600=0.5). The culture solution was left on ice for 10 minutes and then centrifuged at 7000 g for 10 minutes at 4° C. The cell pellets were washed with an electroporation buffer solution three times, and then resuspended in 2 ml of the same buffer solution to manufacture cells for transformation. To 500 μl of the thus prepared cells for transformation, 2.0 μg of pGS1-E1AB plasmid prepared in <3-1> was added followed by electroporation (4 mm cuvette, 2.5 kV, ∞Ω, 25 μF) using a Gene Pulser II manu-

TABLE 3

| SEQ ID NO: 4 | ATGAACTCTAAAATAATTAGATTTGAAAATTTAAGGTCATTCTTTAAAGATGGGATGACAATTATGA<br>TTGGAGGTTTTTTAAACTGTGGCACTCCAACCAAATTAATTGATTTTTTAGTTAATTTAAATATAAA<br>GAATTTAACGATTATAAGTAATGATACATGTTATCCTAATACAGGTATTGGTAAGTTAATATCAAAT<br>AATCAAGTAAAAAGCTTATTGCTTCATATATAGGCAGCAACCCAGATACTGGCAAAAAACTTTTTA<br>ATAATGAACTTGAAGTAGAGCTCTCTCCCCAAGGAACTCTAGTGGAAAGAATACGTGCAGGCGGATC<br>TGGCTTAGGTGGTGTACTAACTAAAACAGGTTTAGGAACTTTGATTGAAAAAGGAAAGAAAAAAATA<br>TCTATAAATGGAACGGAATATTTGTTAGAGCTACCTCTTACAGCCGATGTAGCATTAATTAAAGGTA<br>GTATTGTAGATGAGGCCGGAAACACCTTCTATAAAGGTACTACTAAAAACTTTAATCCCTATATGGC<br>AATGGCAGCTAAAACCGTAATAGTTGAAGCTGAAAATTTAGTTAGCTGTGAAAAACTAGAAAAGGAA<br>AAAGCAATGACCCCCGAGTTCTTATAAATTATATAGTAAGGAGCCTGCATAAAATGATTAATGAT<br>AAAAACCTAGCGAAAGAAATAATAGCCAAAAGAGTTGCAAGAGAATTAAAAAATGGTCAACTTGTAA<br>ACTTAGGTGTAGGTCTTCCTACCATGGTTGCAGATTATATACCAAAAAATTTCAAAATTACTTTCCA<br>ATCAGAAAACGGAATAGTTGGAATGGGCGCTAGTCCTAAAATAAATGAGGCAGATAAAGATGTAGTA<br>AATGCAGGAGGAGACTATACAACAGTACTTCCTGACGGCACATTTTTCGATAGCTCAGTTTGCTTTT<br>CACTAATCCGTGGTGGTCACGTAGATGTTACTGTTTTAGGGGCTCTCCAGGTAGATGAAAAGGGTAA<br>TATAGCCAATTGGATTGTTCCTGGAAAAATGCTCTCTGGTATGGGTGGAGCTATGGATTTAGTAAAT<br>GGAGCTAAGAAAGTAATAATTGCAATGAGACATACAAATAAAGGTCAACCTAAAATTTTAAAAAAAT<br>GTACACTTCCCCTCACGGCAAAGTCTCAAGCAAATCTAATTGTAACAGAACTTGGAGTAATTGAGGT<br>TATTAATGATGGTTTACTTCTCACTGAAATTAATAAAAACACAACCATTGATGAAATAAGGTCTTTA<br>ACTGCTGCAGATTTACTCATATCCAATGAACTTAGACCCATGGCTGTTTAA |
|---|---|
| SEQ ID NO: 5 | CtfAB-UP-BglII: 5'-CACAGATCTATGAACTCTAAAATAATTAGATTTG-3' |
| SEQ ID NO: 6 | CtfAB-DN-EcoRI: 5'-CACGAATTCTTAAACAGCCATGGGTCTAAGTTCATTGGATATGA-3' |
| SEQ ID NO: 7 | THL-UP-XhoI: 5'-ATAAAGCTTAGAATGAAGTTTCTTATGCACAAGTATTTTTTATTAC-3' | factured by Bio-Rad Corporation. Thereafter, the cells were cultured anaerobically in a medium with antibiotics to obtain transformed strain TM2-1-C (pGS1-E1AB).

As a control experiment, pGS1-E1AB plasmid was added to strain ABKO, which was then subjected to electroporation to prepare ABKO (pGS1-E1AB).

<Experimental Example 4> Production of Biobutanol Using Continuous Cultivation

Strain TM2-1-C (pGS1-E1AB) manufactured in <3-2> was evaluated for biobutanol productivity using mixed sugars. This experiment intended to identify butanol productivity of the strain using mixed sugars by continuous cultivation of strain TM2-1-C (E1AB) using the lignocellulosic hydrolysate including the mixed sugars.

A feed solution for performing fed-batch fermentation was prepared as follows. First, to the concentrate of lignocellulosic hydrolysate prepared previously in which the concentration of mixed sugars is about 200 g/L, 3% (wt/v) corn steep liquor, a liquid medium ($MgSO_4 \cdot 7H_2O$, 0.017 g/L $MnSO_4 \cdot 5H_2O$, 0.01 g/L, $FeSO_4 \cdot 7H_2O$, 1 g/L NaCl) and water were added such that final sugar concentration was adjusted to about 150 g/L, thereby preparing a feed solution. The feed solution was injected into an incubator by adjusting the final glucose concentration to 2 g/L or less. Glass bottles including the feed solution were linked to a fermenter by a silicone tube, followed by providing a pump which allows continuous glucose injection. With a time interval of 1-1.5 hours, the concentration of glucose was measured by HPLC, and accordingly the speed of injecting glucose solution was adjusted. When the concentration of glucose is maintained at 2 g/L or less, the amount of sugars lost with discharged culture solution during continuous fermentation as set forth below is minimized, thereby enhancing yield. When the concentration of sugars in the culture solution is high and the concentration of sugars lost with discharged culture solution is also high, the amount of sugars to be converted into butanol is generally reduced, thereby reducing yield. Further, when the concentration of glucose is maintained low, metabolism inhibition of other mixed sugars by glucose (CCR, carbon catabolite repression) can be alleviated.

In addition, an incubator for continuous culturing process was manufactured in accordance with Korean patent application no. 10-2012-0038770. First, at upper and lower ends of a 3 L column, a filter having a pore size of about 150 μm was provided in order to prevent loss of an adsorbent, followed by providing a stirrer, and then charging 300 g of an adsorbing agent. Two columns were prepared. These columns were linked to the incubator by a silicone tube, followed by providing a pump, thereby allowing a culture solution to be circulated between the columns. As the inlet and outlet for the columns, 4-way valves were provided such that in the course of culturing, the columns could be subjected to desorption in real time by introducing a solvent for elution when the adsorbent in the columns was saturated with butanol and mixed solvent. In case that the first column was subjected to desorption, the culture solution was provided to the second column such that the culture solution was circulated continuously. The culture solution was circulated from the top to the bottom of the column, but the direction is not particularly limited. Strain TM2-1-C (pGS1-E1AB) was cultured in the incubator manufactured above.

To the incubator, 2.6 L of a medium containing about 50 g/L of the concentrated lignocellulosic hydrolysate was charged. The medium containing the lignocellulosic hydrolysate was inoculated with 600 ml of TM2-1-C (pGS1-E1AB), which had been anaerobically cultured in liquid CGM, to initiate cultivation. After initiation of the cultivation, the culture solution taken from the incubator was transferred to a first column, wherein the culture solution was circulated by passing through the first column with a flow rate of 100 ml/min through a pump when butanol concentration became about 6 g/L to 8 g/L. As the culture solution passed through the first column, the adsorbent was suspended in the culture solution to form a dilute slurry phase, which prevented the culture solution from flocking, thereby passing through the column. Butanol concentration was maintained at 8 g/L or less by taking the culture solution samples just before and after passing through the column and monitoring the concentration. Cultivation was performed by continuous fermentation for 162.5 hours.

Figure 9:
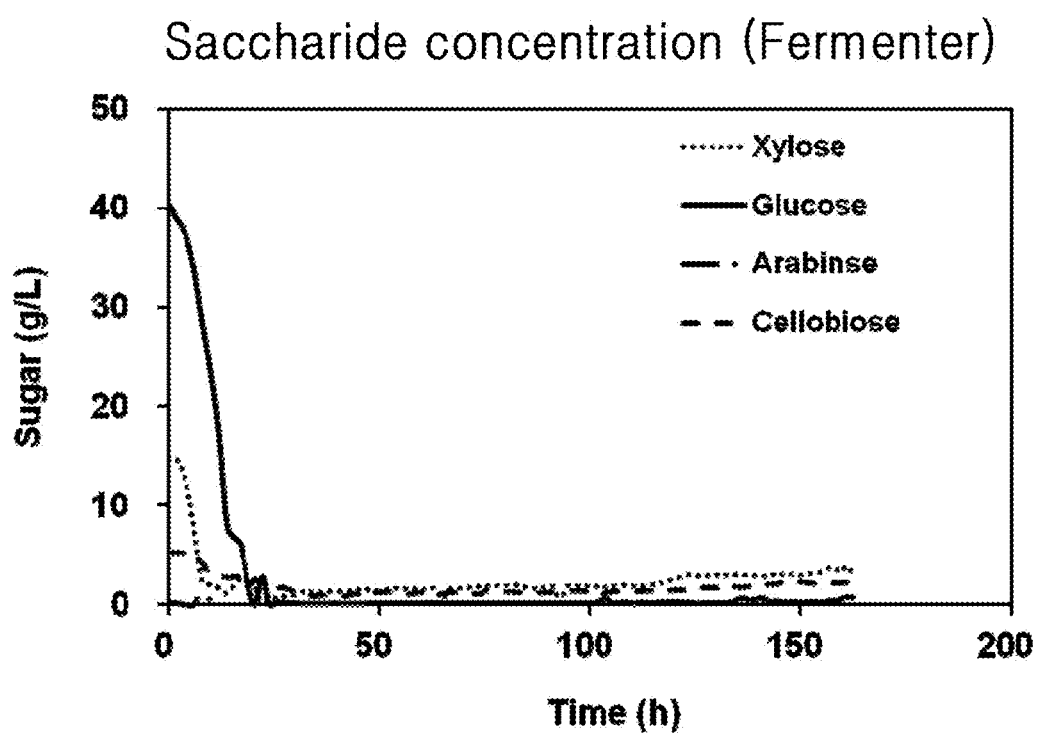
FIG. 9 shows a sugar profile in a medium over fermentation time upon continuous fermentation of a lignocellulosic hydrolysate including mixed sugars for 162.5 hours by TM2-1-C (pGS1-E1AB).

As a result, among mixed sugars introduced as the feed solution, xylose was added up to 957.3 g wherein only about 31 g xylose remained in a remaining culture solution, discharged culture solution and solvent-desorption solution, and the other xylose was converted into mixed solvent (ABE). From this, it can be seen that xylose showed 97% simultaneous co-fermentation. Further, arabinose which is a pentose showed 100% simultaneous co-fermentation. Cellobiose was introduced up to 383.2 g, wherein about 363.8 g of cellobiose was converted into a mixed solvent (ABE) and an amount of about 19.4 g of cellobiose is remained in a remaining culture solution, discharged culture solution and solvent-desorption solution. From this, it can be seen that cellobiose is capable of 95% or more simultaneous co-fermentation (FIG. 9, Table 4).

As a control group, the same experiment was performed using ABKO (pGS1-E1AB). However, since ABKO (pGS1-E1AB) did not have tolerance against microorganism inhibitory substances in the lignocellulosic hydrolysate, cultivation was substantially impossible.

TABLE 4

| Mixed sugars | Total mixed sugars introduced g | Proportion of mixed sugars % | Total amount of remaining sugars g | | Simultaneous co-fermentation ratio |
|---|---|---|---|---|---|
| | | | | % | |
| Glucose | 2607.66 | 65.80 | 7.49 | 0% | 100% |
| Xylose | 957.32 | 24.16 | 30.94 | 3% | 97% |
| Galactose | 0.00 | 0 | 0.00 | — | — |
| Arabinose | 14.83 | 0.37 | 0.00 | 0% | 100% |
| Mannose | 0.00 | 0 | 0.00 | — | — |
| Cellobiose | 383.19 | 9.67 | 19.35 | 5% | 95% |
| Sum | 3963 | | 58 | | |

Total mixed sugars introduced: Mixed sugars introduced as a feed solution

Total amount of remaining sugars: Sugars present in a remaining culture solution, discharged culture solution and solvent-desorption liquid.

Simultaneous co-fermentation ratio={(Total sugars introduced (g)−Total amount of remaining sugars (g))/Total sugars introduced (g)}×100

Discharged culture solution: Fermented liquid removed from the fermenter in proportion to the amount of the feed solution introduced during continuous co-fermentation Solvent-desorption liquid: Liquid generated from desorption of column through steam when an adsorbent is saturated by adsorbing acetone, butanol and ethanol (ABE) as fermentation products Proportion of mixed sugars (%)={(Total amount of each sugars introduced (g)/Total sugars introduced (g)}×100

Ex) Proportion of xylose in mixed sugars={Total amount of xylose introduced 957.32 (g)/Total amount of sugars introduced 3963 (g)}× 100=24.16%

Analysis of fermented products adsorbed to the adsorbent in the column showed that TM2-1-C (pGS1-E1AB) performed simultaneous co-fermentation using mixed sugars as a mixed solvent while maintaining tolerance against inhibitory substances included in the mixed sugars in the lignocellulosic hydrolysate, and thus achieved a yield of 33.9%, productivity of 2.8 g/L/h, and butanol selectivity of 79.3%.

The strain exhibited excellent performance as compared with any other strains capable of simultaneous co-fermentation of mixed sugars reported up to now (Table 5).

TABLE 5

|  | Acetone | Ethanol | Butanol | ABE |
|---|---|---|---|---|
| Produced amount (g) | 148.2 | 129.8 | 1064.6 | 1342.6 |
| Productivity (g/L/h) | 0.3 | 0.3 | 2.2 | 2.8 |
| Yield (based on introduced amount) (%) | 3.7 | 3.3 | 26.9 | 33.9 |
| Selectivity (%) | 11.0 | 9.7 | 79.3 | 100.0 |

<Deposit Number>
International Patent Organism Depositary: Korea Collection for Type Culture (KCTC)
Deposit number: KCTC 12604BP
Deposit date: Jun. 10, 2014

What is claimed is:

1. A microorganism capable of simultaneous co-fermentation of two or more sugars in a lignocellulosic hydrolysate and having the ability to produce butanol, wherein the microorganism is *Clostridium acetobutylicum* TM2-1-C(accession number KCTC 12604BP).

2. The microorganism according to claim 1, wherein the microorganism has tolerance against the lignocellulosic hydrolysate.

3. The microorganism according to claim 1, wherein the microorganism has the ability of simultaneous co-fermentation of glucose and xylose.

4. The microorganism according to claim 1, wherein, when the microorganism is grown under batch conditions in the presence of glucose and xylose, 30% or more of the metabolized sugar is xylose and butanol productivity is 1.0 g/L/h or more.

5. A recombinant microorganism having improved butanol productivity in comparison to *Clostridium acetobutylicum* TM2-1-C, wherein the recombinant microorganism is prepared from the *Clostridium acetobutylicum* TM2-1-C by promoting a pathway converting butyryl-CoA into butanol or a pathway converting butyrate into butyryl-CoA, the pathway converting butyryl-CoA into butanol is promoted by increasing aldehyde/alcohol dehydrogenase activity in comparison to *Clostridium acetobutylicum* TM2-1-C by introduction of an adhE gene encoding an aldehyde/alcohol dehydrogenase, and the pathway converting butyrate into butyryl-CoA is promoted by increasing CoA transferase activity in comparison to *Clostridium acetobutylicum* TM2-1-C by introduction of a ctfAB gene encoding a CoA transferase.

6. The recombinant microorganism according to claim 5, wherein the recombinant microorganism has the ability of simultaneous co-fermentation of two or more sugars in a lignocellulosic hydrolysate.

7. The recombinant microorganism according to claim 5, wherein the recombinant microorganism has the ability of simultaneous co-fermentation of glucose and at least one sugar selected from the group consisting of xylose, arabinose and cellobiose.

8. The recombinant microorganism according to claim 5, wherein butanol selectivity is 70% or more when the recombinant microorganism is grown under fed-batch conditions.

9. The recombinant microorganism according to claim 5, wherein acetone selectivity is less than 20% when the recombinant microorganism is grown under fed-batch conditions.

10. The recombinant microorganism according to claim 5, wherein ethanol selectivity is less than 20% when the recombinant microorganism is grown under fed-batch conditions.

11. The recombinant microorganism according to claim 5, wherein butanol productivity is 0.5 g/L/h or more when the recombinant microorganism is grown under fed-batch conditions.

12. A method for producing butanol, comprising:
preparing a medium comprising two or more sugars;
inoculating the medium with the microorganism according to claim 1; and
culturing the microorganism.

13. A method for producing butanol, comprising:
preparing a medium including two or more sugars;
inoculating the medium with the recombinant microorganism according to claim 5; and
culturing the recombinant microorganism.

14. The method according to claim 13, wherein the two or more sugars comprise glucose and at least one sugar selected from the group consisting of xylose, arabinose and cellobiose.

15. The method according to claim 13, wherein the medium comprises a lignocellulosic hydrolysate.

* * * * *

SEQUENCE LISTING

```
<160> NUMBER OF SEQ ID NOS: 7

<210> SEQ ID NO 1
<211> LENGTH: 2589
<212> TYPE: DNA
<213> ORGANISM: Clostridium acetobutylicum

<400> SEQUENCE: 1
atgaaagtca caacagtaaa ggaattagat gaaaaactca aggtaattaa agaagctcaa      60
aaaaaattct cttgttactc gcaagaaatg gttgatgaaa tctttagaaa tgcagcaatg     120
gcagcaatcg acgcaaggat agagctagca aaagcagctg ttttggaaac cggtatgggc     180
ttagttgaag acaaggttat aaaaaatcat tttgcaggcg aatacatcta taacaaatat     240
aaggatgaaa aaacctgcgg tataattgaa cgaaatgaac cctacggaat tacaaaaata     300
gcagaaccta taggagttgt agctgctata atccctgtaa caaacccac atcaacaaca      360 atatttaaat ccttaatatc ccttaaaact agaaatggaa ttttcttttc gcctcaccca     420
agggcaaaaa aatccacaat actagcagct aaaacaatac ttgatgcagc cgttaagagt     480
ggtgcccggg aaaatataat aggttggata gatgaaacctt caattgaact aactcaatat     540
ttaatgcaaa aagcagatat aaccccttgca actggtggtc cctcactagt taaatctgct     600
tattcttccg gaaaaccagc aataggtgtt ggtccgggta cacccccagt aataattgat     660
gaatctgctc atataaaaat ggcagtaagt tcaattatat tatccaaaac ctatgataat     720
ggtgttatat gtgcttctga acaatctgta atagtcttaa aatccatata taacaaggta     780
aaagatgagt tccaagaaag aggagcttat ataataaaga aaaacgaatt ggataaagtc     840
cgtgaagtga ttttttaaaga tggatccgta aaccctaaaa tagtcggaca gtcagcttat     900
actatagcag ctatggctgg cataaaagta cctaaaacca caagaatatt aataggagaa     960
gttacctcct taggtgaaga agaaccttttt gcccacgaaa aactatctcc tgtttttggct    1020 atgtatgagg ctgacaattt tgatgatgct ttaaaaaaag cagtaactct aataaactta    1080
ggaggcctcg gccatacctc aggaatatat gcagatgaaa taaaagcacg agataaaata    1140
gatagattta gtagtgccat gaaaaccgta agaaccttttg taaatatccc aacctcacaa    1200
ggtgcaagtg gagatctata taatttttaga ataccacctt cttttcacgct tggctgcgga    1260 tttggggag gaaattctgt ttccgagaat gttggtccaa aacatctttt gaatattaaa    1320
accgtagctg aaaggagaga aaacatgctt tggtttagag ttccacataa agtatatttt    1380
```

```
aagttcggtt gtcttcaatt tgctttaaaa gatttaaaag atctaaagaa aaaaagagcc      1440
tttatagtta ctgatagtga cccctataat ttaaactatg ttgattcaat aataaaaata      1500
cttgagcacc tagatattga ttttaaagta tttaataagg ttggaagaga agctgatctt      1560
aaaaccataa aaaaagcaac tgaagaaatg tcctccttta tgccagacac tataatagct      1620
ttaggtggta cccctgaaat gagctctgca aagctaatgt gggtactata tgaacatcca      1680
gaagtaaaat ttgaagatct tgcaataaaa tttatggaca taagaaagag aatatatact      1740
ttcccaaaac tcggtaaaaa ggctatgtta gttgcaatta caacttctgc tggttccggt      1800
tctgaggtta ctccttttgc tttagtaact gacaataaca ctggaaataa gtacatgtta      1860
gcagattatg aaatgacacc aaatatggca attgtagatg cagaacttat gatgaaaatg      1920
ccaaagggat taaccgctta ttcaggtata gatgcactag taaatagtat agaagcatac      1980
acatccgtat atgcttcaga atacacaaac ggactagcac tagaggcaat acgattaata      2040
tttaaatatt tgcctgaggc ttacaaaaac ggaagaacca atgaaaaagc aagagagaaa      2100
atggctcacg cttcaactat ggcaggtatg gcatccgcta atgcatttct aggtctatgt      2160
cattccatgg caataaaatt aagttcagaa cacaatattc ctagtggcat tgccaatgca      2220
ttactaatag aagaagtaat aaaatttaac gcagttgata atcctgtaaa acaagcccct      2280
tgcccacaat ataagtatcc aaacaccata tttagatatg ctcgaattgc agattatata      2340
aagcttggag gaaatactga tgaggaaaag gtagatctct taattaacaa aatacatgaa      2400
ctaaaaaaag ctttaaatat accaacttca ataaggatg caggtgtttt ggaggaaaac      2460
ttctattcct cccttgatag aatatctgaa cttgcactag atgatcaatg cacaggcgct      2520
aatcctagat ttcctcttac aagtgagata aagaaatgt atataaattg tttttaaaaaa      2580 caaccttaa                                                             2589

<210> SEQ ID NO 2
<211> LENGTH: 39
<212> TYPE: DNA
<213> ORGANISM: Artificial
<220> FEATURE:
<223> OTHER INFORMATION: a primer AdhE1-UP-PstI for amplifying adhE1
      gene

<400> SEQUENCE: 2
cacctgcaga tgaaagtcac aacagtaaag gaattagat                             39

<210> SEQ ID NO 3
<211> LENGTH: 41
<212> TYPE: DNA
<213> ORGANISM: Artificial
<220> FEATURE:
<223> OTHER INFORMATION: a primer AdhE1-DN-XhoI for amplifying adhE1
      gene

<400> SEQUENCE: 3
cacctcgagt taaggttgtt ttttaaaaca atttatatac a                          41

<210> SEQ ID NO 4
<211> LENGTH: 1324
<212> TYPE: DNA
<213> ORGANISM: Clostridium acetobutylicum

<400> SEQUENCE: 4
atgaactcta aataattag atttgaaaat ttaaggtcat tctttaaaga tgggatgaca      60
attatgattg gaggtttttt aaactgtggc actccaacca aattaattga ttttttagtt      120
```

```
aatttaaata taaagaattt aacgattata agtaatgata catgttatcc taatacaggt      180
attggtaagt taatatcaaa taatcaagta aaaaagctta ttgcttcata tataggcagc      240
aacccagata ctggcaaaaa acttttaat aatgaacttg aagtagagct ctctccccaa       300
ggaactctag tggaaagaat acgtgcaggc ggatctggct taggtggtgt actaactaaa      360
acaggtttag gaactttgat tgaaaaagga agaaaaaaa tatctataaa tggaacggaa       420
tatttgttag agctacctct tacagccgat gtagcattaa ttaaaggtag tattgtagat      480
gaggccggaa acaccttcta taaaggtact actaaaaact ttaatcccta tatggcaatg      540
gcagctaaaa ccgtaatagt tgaagctgaa aatttagtta gctgtgaaaa actagaaaag      600
gaaaaagcaa tgaccccgg agttcttata aattatatag taaaggagcc tgcataaaat       660
gattaatgat aaaaacctag cgaaagaaat aatagccaaa agagttgcaa gagaattaaa      720
aaatggtcaa cttgtaaact taggtgtagg tcttcctacc atggttgcag attatatacc      780
aaaaaatttc aaaattactt tccaatcaga aaacggaata gttggaatgg gcgctagtcc      840
taaaataaat gaggcagata agatgtagt aaatgcagga ggagactata caacagtact       900
tcctgacggc acattttcg atagctcagt ttcgttttca ctaatccgtg gtggtcacgt       960
agatgttact gttttagggg ctctccaggt agatgaaaag ggtaatatag ccaattggat     1020
tgttcctgga aaatgctct ctggtatggg tggagctatg gatttagtaa atggagctaa      1080
gaaagtaata attgcaatga gacatacaaa taaaggtcaa cctaaaattt taaaaaaatg     1140
tacacttccc ctcacggcaa agtctcaagc aaatctaatt gtaacagaac ttggagtaat     1200
tgaggttatt aatgatggtt tacttctcac tgaaattaat aaaaacacaa ccattgatga     1260
aataaggtct ttaactgctg cagatttact catatccaat gaacttagac ccatggctgt     1320
ttaa                                                                 1324

<210> SEQ ID NO 5
<211> LENGTH: 34
<212> TYPE: DNA
<213> ORGANISM: Artificial
<220> FEATURE:
<223> OTHER INFORMATION: a primer CtfAB-UP-BglII for amplifying ctfAB
      gene

<400> SEQUENCE: 5
cacagatcta tgaactctaa aataattaga tttg                                   34

<210> SEQ ID NO 6
<211> LENGTH: 44
<212> TYPE: DNA
<213> ORGANISM: Artificial
<220> FEATURE:
<223> OTHER INFORMATION: a primer CtfAB-DN-EcoRI for amplifying ctfAB
      gene

<400> SEQUENCE: 6
cacgaattct aaacagcca tgggtctaag ttcattggat atga                         44

<210> SEQ ID NO 7
<211> LENGTH: 46
<212> TYPE: DNA
<213> ORGANISM: Artificial
```

```
<220> FEATURE:
<223> OTHER INFORMATION: a primer THL-UP-XhoI  for amplifying ctfAB gene

<400> SEQUENCE: 7
ataaagctta gaatgaagtt tcttatgcac aagtattttt tattac                    46
```